United States Patent
Klausing et al.

(10) Patent No.: US 9,856,529 B2
(45) Date of Patent: *Jan. 2, 2018

(54) METHOD FOR NUCLEOTIDE DETECTION

(71) Applicant: Illumina, Inc., San Diego, CA (US)

(72) Inventors: Kay Klausing, San Diego, CA (US); Min-Jui Richard Shen, Poway, CA (US); John Moore, San Diego, CA (US); Vincent Peter Smith, Nr Saffron Walden (GB); Kevin Hall, Nr Saffron Walden (GB)

(73) Assignee: ILLUMINA, INC., San Diego, CA (US)

( * ) Notice: Subject to any disclaimer, the term of this patent is extended or adjusted under 35 U.S.C. 154(b) by 208 days.

This patent is subject to a terminal disclaimer.

(21) Appl. No.: 14/729,376

(22) Filed: Jun. 3, 2015

(65) Prior Publication Data
US 2015/0259737 A1 Sep. 17, 2015

Related U.S. Application Data

(63) Continuation of application No. 13/018,255, filed on Jan. 31, 2011, now Pat. No. 9,115,353.

(51) Int. Cl.
*C12Q 1/68* (2006.01)
*C40B 20/04* (2006.01)
(Continued)

(52) U.S. Cl.
CPC ....... *C12Q 1/6874* (2013.01); *C12N 15/1003* (2013.01); *C12Q 1/6832* (2013.01); *C40B 20/04* (2013.01); *C12Q 1/6869* (2013.01)

(58) Field of Classification Search
CPC .. C12Q 1/6874; C12Q 1/6832; C12Q 1/6869; C12N 15/1003; C40B 20/04
See application file for complete search history.

(56) References Cited

U.S. PATENT DOCUMENTS

| 2007/0161017 A1 | 7/2007 | Eid et al. |
| 2008/0280773 A1 | 11/2008 | Fedurco et al. |

(Continued)

FOREIGN PATENT DOCUMENTS

| WO | 01/94630 | 12/2001 |
| WO | 2006/064199 | 6/2006 |
| WO | 2007/064905 | 6/2007 |

OTHER PUBLICATIONS

Bentley, et al., "Accurate whole human genome sequencing using reversible terminator chemistry", Nature, vol. 456, No. 7218, Nov. 6, 2008, 53-59.
(Continued)

*Primary Examiner* — Jeremy C Flinders

(57) ABSTRACT

A method of inhibiting light-induced degradation of nucleic acids includes irradiating a portion of the nucleic acids in the presence of a detection solution comprising a polyphenolic compound. A method of detecting a nucleic acid having a fluorescent tag includes irradiating at least a portion of the nucleic acid with light of a suitable wavelength to induce a fluorescence emission and detecting the fluorescence emission. Optionally, the polyphenolic compound is gallic acid, a lower alkyl ester thereof, or mixtures thereof. A kit includes one or more nucleotides, an enzyme capable of catalyzing incorporation of the nucleotides into a nucleic acid strand and a polyphenolic compound suitable for preparing a detection solution.

20 Claims, 5 Drawing Sheets

(51) Int. Cl.
   *C12N 15/10*   (2006.01)
   *C12Q 1/48*   (2006.01)

(56) References Cited

U.S. PATENT DOCUMENTS

2010/0143945 A1   6/2010   Khoshnan
2010/0221716 A1   9/2010   Flusberg et al.
2010/0323350 A1   12/2010   Gordon

OTHER PUBLICATIONS

Brand-Williams, et al., Lebensm.-Wiss.u.Technol. 28, 1995, 25-30.
Breen, et al., Free Radical Biology and Medicine, 18(6), 1995, 1033-1077.
Cooke, et al., "Oxidative DNA damage: mechanisms, mutation, and disease", FASEB J. 17(10), 1195-1214.
Coste, F. et al., "Bacterial base excision repair enzyme Fpg recognizes bulky N7-substituted-FapydG lesion via unproductive binding mode", Chemistry & Biology, vol. 15, Issue 7, Jul. 21, 2008, 706-717.
Crispo, et al., "Protective effects of methyl gallate on H2O2-induced apoptosis in PC12 cells", Biochemical and Biophysical Research Communications, 2010, 393:773-778.
Dahl, et al., "Some Prevalent Biomolecules as Defenses Against Singlet Oxygen Damage", Photochem. Photobiol. 47(3), 1988, 357-362.
Elsner, et al., DNA 8, 1989, 697-701.
European Search Report, , "Application No. 12741790.5", dated Aug. 21, 2014.
Gandhi, N.M. et al., "Protection of DNA and membrane from gamma radiation induced damage by gallic acid", Molecular and Cellular Biochemistry, vol. 278, Oct. 2005, 111-117.
"Fluorescence-based assay for reactive oxygen species: a protective role for creatinine", FASEB J 2, 1988, 2487-2491.
Labieniec, Magdalena et al., "Oxidatively modified proteins and DNA in digestive gland cells of the fresh-water mussel Uniotumidus in the presence of tannic acid and its derivatives", Mutation Research; vol. 603, No. 1, XP002728247, ISSN: 0027-5107, Jan. 31, 2006, 48-55.
McMurray, et al., Genome Res., 8, 1998, 562-566.
Nalini, Mistry et al., "Immunochemical detection of glyoxal DNA damage", Free Radical Biology & Medicine, vol. 26, No. 9-10, XP055133672, ISSN: 0891-5849, May 1, 1999, 1267-1273.
Park, EM , "Assay of excised oxidative DNA lesions: Isolation of 8-oxoguanine and its nucleoside derivatives from biological fluids with a monoclonal antibody column", Proc. Natl. Acad. Sci. USA vol. 89, Medical Sciences, Apr. 1992, 3375-3379.
Sakagami, et al., "The interaction between two antioxidants, sodium ascorbate and gallic acid: radical intensity and apoptosis induction", Anticancer Res., 16(3A), 1996, 1231-1234.
Soultanakis, Rebecca , "Fluorescence detection of 8-oxoguanine in nuclear and mitochondrial DNA and cultured cells using a recombinant Fab and confocal scanner laser microscopy", Free Radical Biology & Medicine, vol. 28, No. 6, XP055133671; ISSN: 0891-5849, Mar. 1, 2000, 987-998.
Sun, N-K. et al., "Damaged DNA-binding protein 2 (DDB2) protects against UV irradiation in human cells and *Drosophila*", Journal of biomedical Science, vol. 17, No. 27, Apr. 17, 2010, 1-14.
Yen, G-C. et al., "Antioxidant and pro-oxidant properties of ascorbic acid and gallic acid", Food Chemistry, vol. 79, No. 3, Nov. 2002, 307-313.

METHOD FOR NUCLEOTIDE DETECTION

The present invention relates generally to nucleic acid detection, and more specifically to iterative nucleic acid detection.

BACKGROUND OF THE INVENTION

Numerous methods used to detect and characterize nucleic acid structures employ tagging schemes that rely on electromagnetic radiation (EM) emission of an excited state light-absorbing chromophore. Examples of such photoluminescent processes include phosphorescence and fluorescence emission. Fluorescence detection, for example, has been used in DNA sequencing to great effect due, in part, to the high degree of sensitivity allowing single molecule detection.

Performing iterative fluorescent detection steps in an array context, such as sequencing by synthesis, can cause fluorescence signal intensity loss (see, for example, Fedurco et al. WO2006/064199). This problem was addressed, in part, by the addition of ascorbate to a detection solution to increase the number of useful detection cycles from about eight to ten cycles, in the absence of ascorbate, to about 25 cycles in the presence of ascorbate. The possible mechanisms that underlie this signal loss are numerous, and can include cleavage of individual nucleic acid members from the support.

There are a number of pathways by which nucleic acid damage can occur during irradiation in fluorescence detection. Fluorescence emission normally occurs with the emission of light of a longer wavelength (lower energy), than the original irradiating source. However, under conditions in which intense EM radiation is being absorbed by the fluorophore, such as in laser-induced fluorescence (LIF), it is possible for a molecule to absorb two photons, which can lead to the emission of higher energy radiation of smaller wavelengths than the original excitation source. This multiple photon absorption can cause the fluorophore to emit EM radiation in the UV-visible region which can contribute to nucleic acid base dimerization and/or the generation of reactive oxygen species.

For example, it has been indicated that exposure of whole cells to ultraviolet (UV) radiation can cause DNA damage via the direct photochemical [2+2] photocycloaddition reaction of thymine or cytosine to provide cyclobutane pyrimidine dimers, such as TT, TC, and CC. Such direct photocycloaddition reactions can occur in the UV B and UV C regions which extend from about 100 nm to about 315 nm.

In the UV A region through a portion of the visible region, spanning from about 315 nm to about 500 nm, a complex mixture of indirect mechanisms can also cause DNA damage through photosensitization of other cellular components. Such indirect mechanisms can result in pyrimidine dimer formation and oxidative DNA modification via reactive species such as singlet oxygen, superoxide anion, and iron-promoted hydroxyl radical formation. Finally, it also has also been indicated that reactive singlet oxygen can be generated by fluorescence quenching of an excited state fluorophore by triplet oxygen. Any combination of direct or indirect pyrimidine dimerization and nucleic acid damage due to various reactive oxygen species observed in whole cells can be the underlying cause of fluorescence signal intensity loss observed in the array context.

There is a need to further reduce fluorescent signal intensity loss for applications in sequencing by synthesis to facilitate sequencing of long nucleotide sequences, including sequences of 50, 75, 100, 200, and 500 nucleotides or more. Moreover, solutions to fluorescent signal intensity loss in the context sequencing by synthesis are readily applicable to other nucleic acid detection platforms that employ multiple irradiation steps. The present invention satisfies this need and provides related advantages as well.

SUMMARY OF THE INVENTION

Provided herein is a method of inhibiting light-induced degradation of nucleic acids. The method includes irradiating a portion of said nucleic acids in the presence of a detection solution comprising a polyphenolic compound. Also provided is a method of detecting a nucleic acid having a fluorescent tag. The method includes irradiating at least a portion of said nucleic acid with light, wherein said light comprises a suitable wavelength to induce a fluorescence emission, detecting the fluorescence emission. Optionally, the polyphenolic compound is gallic acid, a lower alkyl ester thereof, or mixtures thereof.

In addition, provided herein is a kit comprising one or more nucleotides, an enzyme capable of catalyzing incorporation of the nucleotides into a nucleic acid strand and a polyphenolic compound suitable for preparing a detection solution.

DETAILED DESCRIPTION OF THE INVENTION

The present invention is directed, in part, to a method of inhibiting light-induced degradation of nucleic acids during a detection step that includes irradiating a portion of the nucleic acids in the presence of a detection solution having a polyphenolic compound. The presence of the polyphenolic compound in the detection solution inhibits the amount of light-induced degradation of the nucleic acids.

The present invention is also directed, in part, to a method of detecting a nucleic acid having a fluorescent tag that includes a) irradiating the nucleic acid with light having a suitable wavelength to induce a fluorescence emission; b) detecting the fluorescence emission; and repeating these steps iteratively. The irradiating step is carried out in the presence of a detection solution that includes a polyphenolic compound and serves to reduce light-induced degradation of the nucleic acid.

Figure 1:
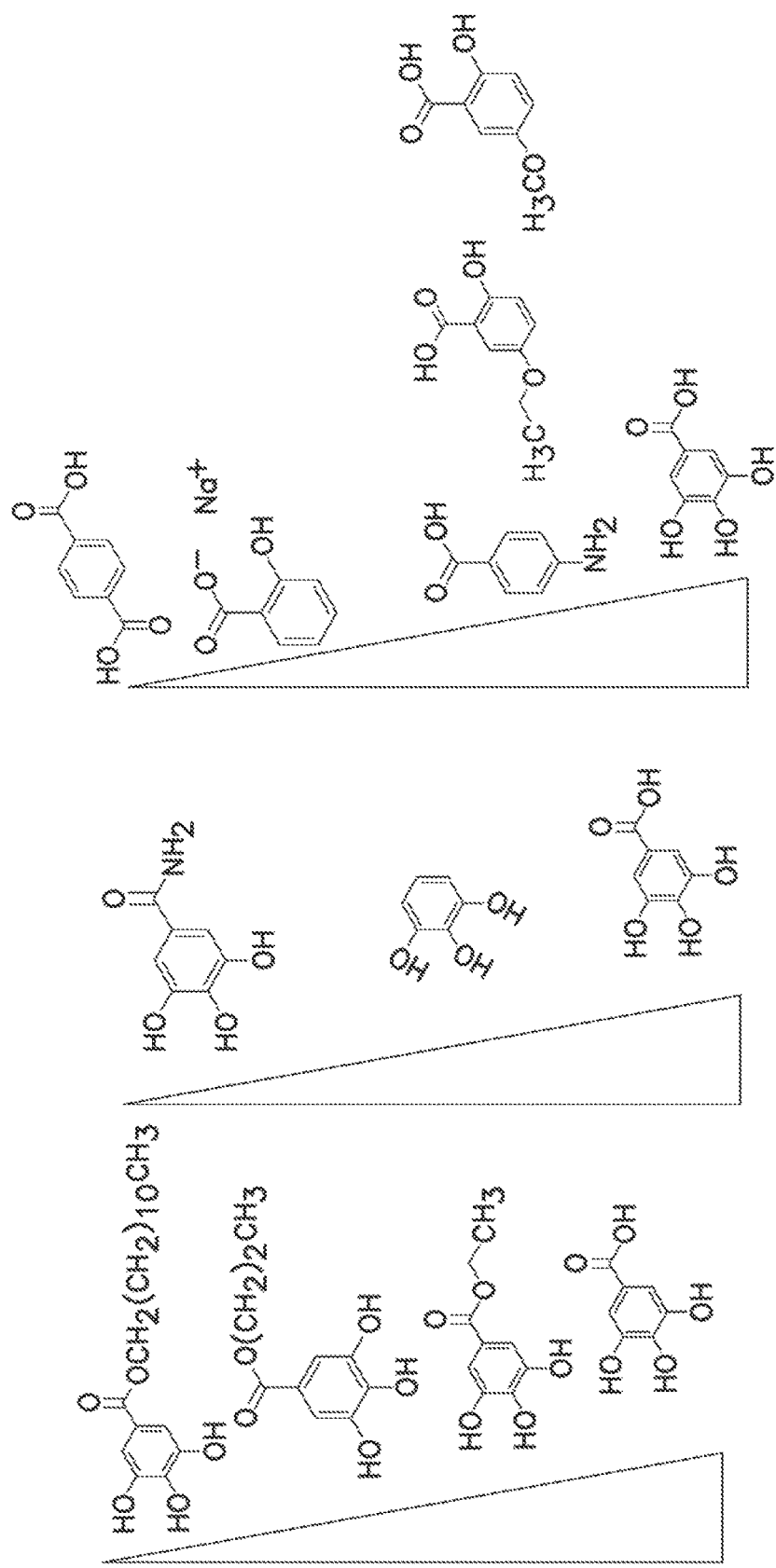
FIG. 1 shows a graphic representation of the relative effectiveness of representative polyphenolic compounds, and related structures, in providing protection from light-induced degradation. Increased effectiveness is shown from top (least) to bottom (most).
Figure 2:
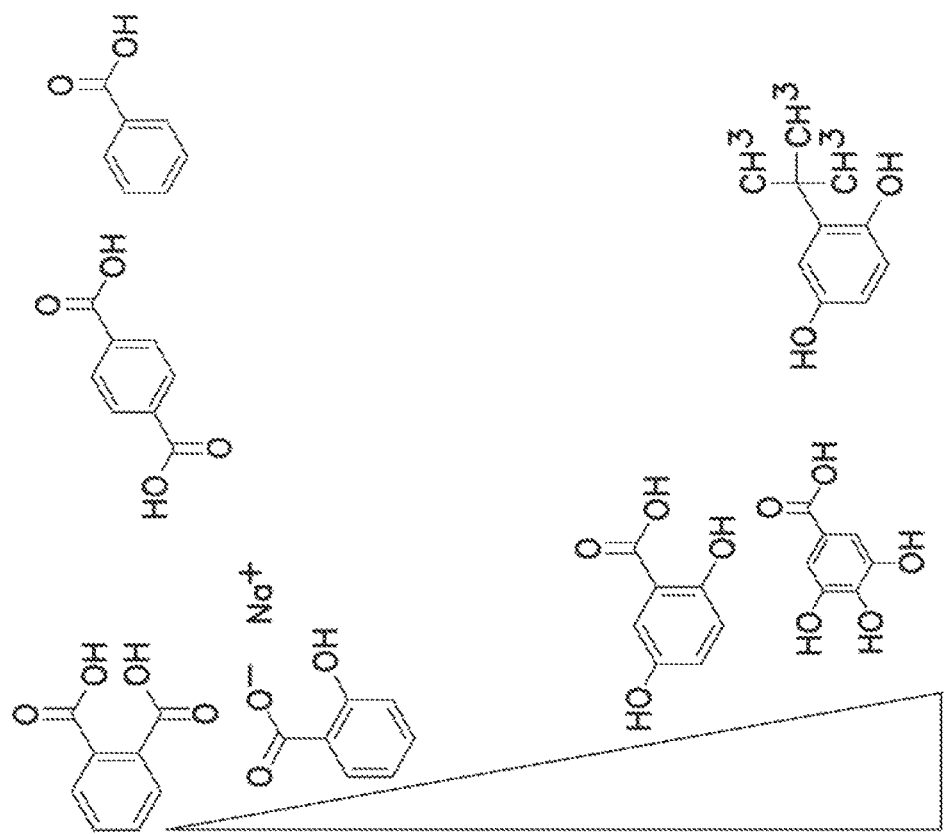
FIG. 2 shows a graphic representation of the relative effectiveness of representative polyphenolic compounds, and related structures, in providing protection from light-induced degradation. Increased effectiveness is shown from top (least) to bottom (most).
Figure 2:
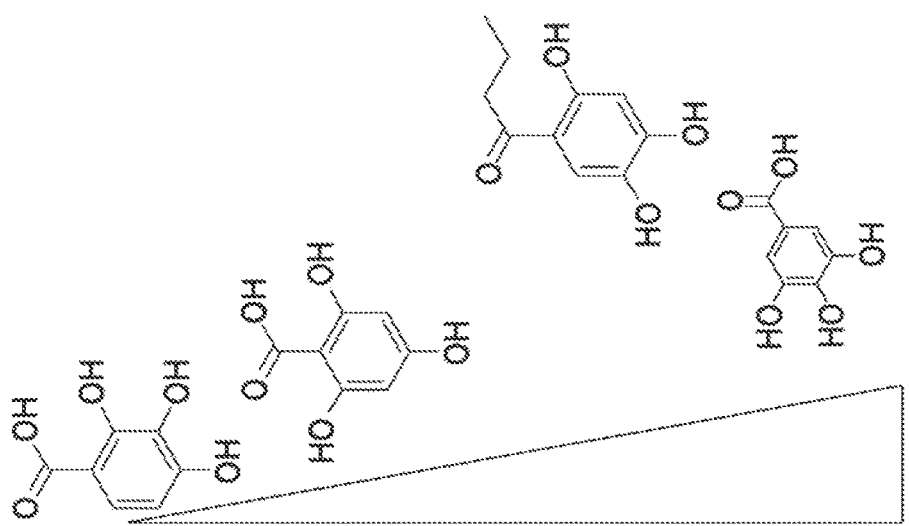

Polyphenolic compounds, exemplified in FIGS. 1 and 2 and Tables 1 and 2, used in detection solutions provide protection to nucleic acids from light-induced degradation that can occur during detection steps performed in various assays, including for example, base calling in sequencing by synthesis. The polyphenolic compounds disclosed herein have been identified as successfully ameliorating the effects of light-induced degradation among numerous other classes of compounds that can shut down plausible mechanistic degradation pathways. Such compounds classes include, without limitation, hydroxyl radical quenchers, reactive oxygen species (singlet oxygen, superoxide anion) quenchers, oxygen scavengers, triplet state quenchers, and hole quenchers.

Figure 4:
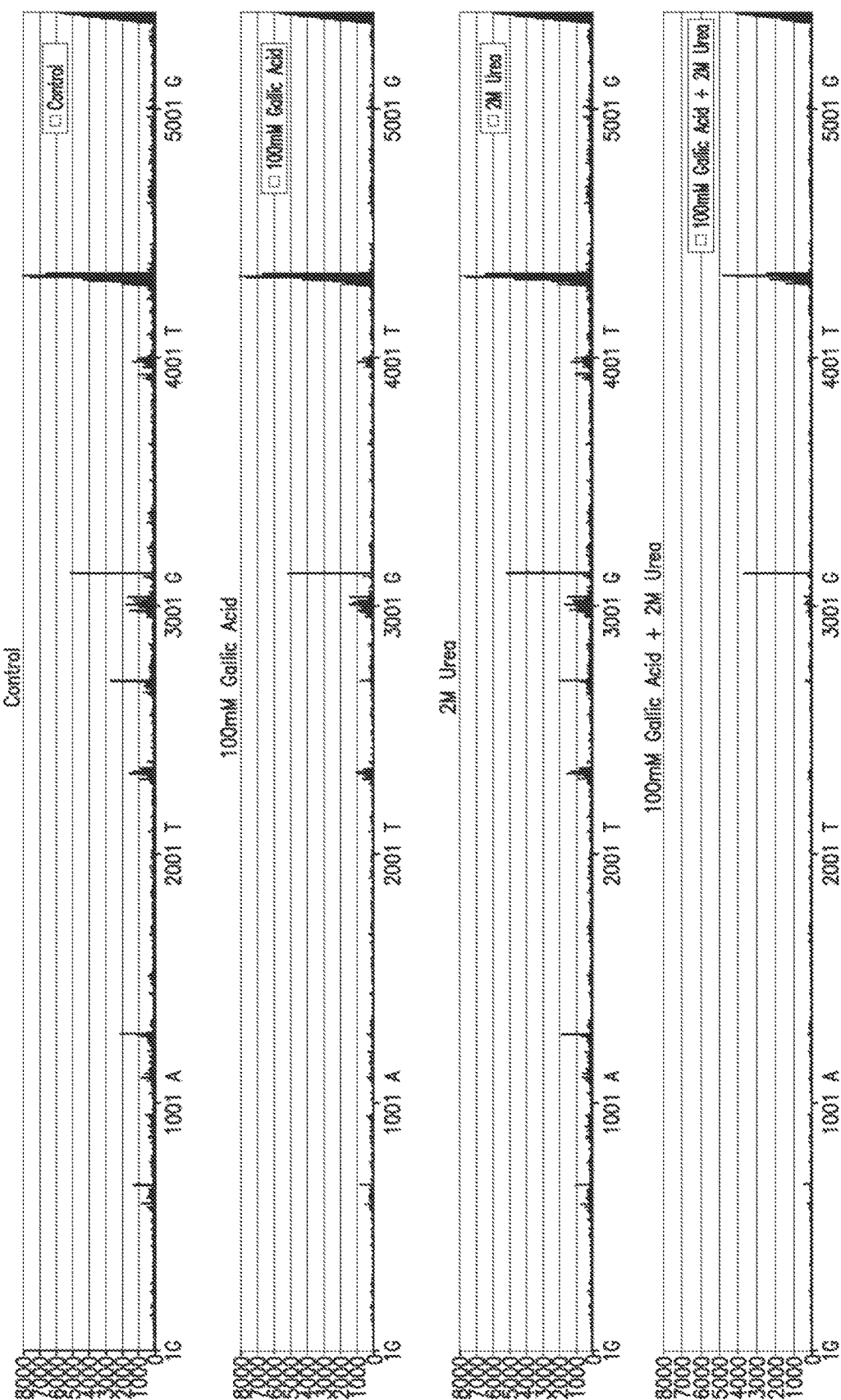
FIG. 4 shows coverage plots in a control sequence, in the presence of gallic acid, in the presence of urea, and in the presence of gallic acid and urea, over 75 cycles.
Figure 5:
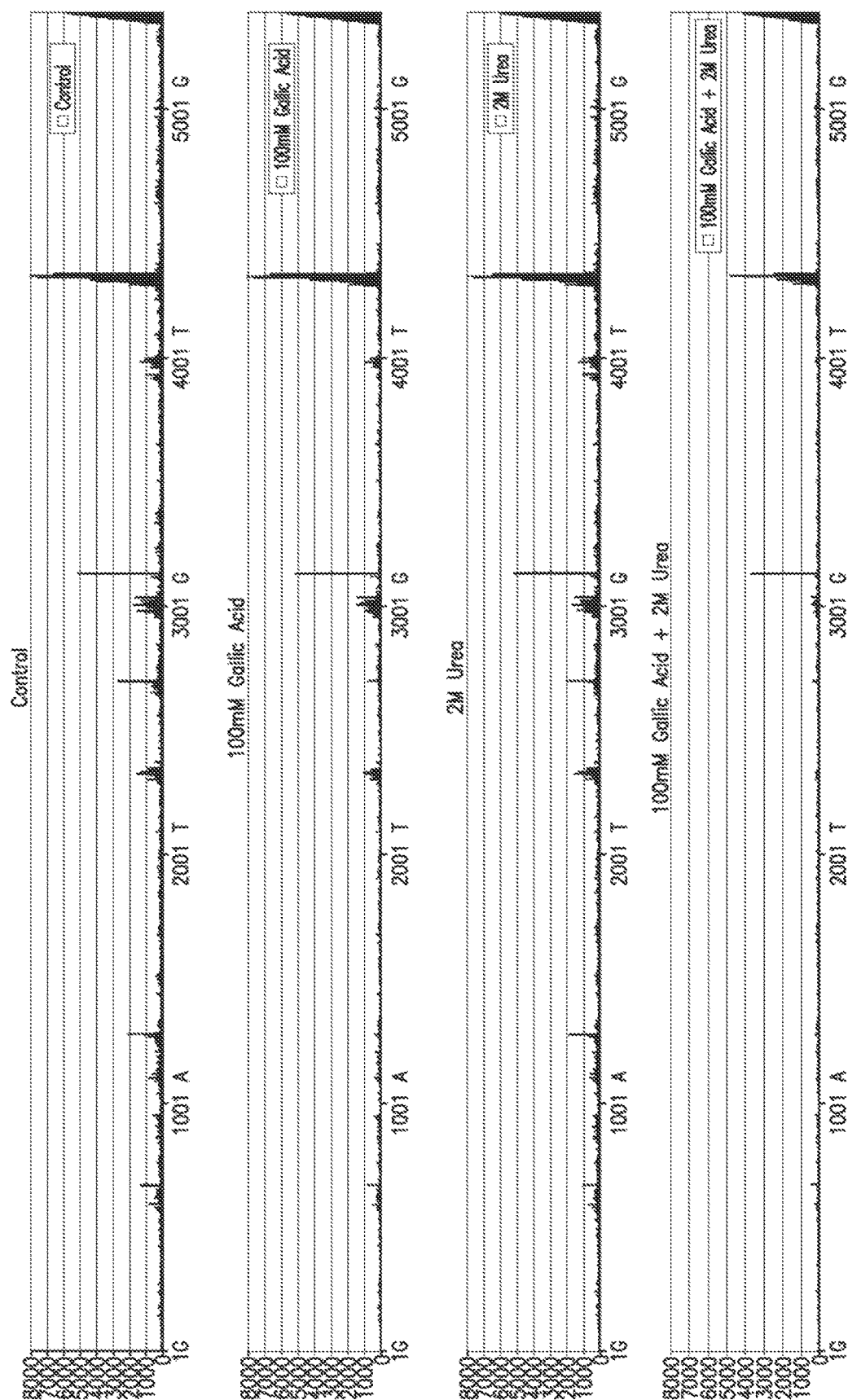
FIG. 5 shows coverage plots in a control sequence, in the presence of gallic acid, in the presence of urea, and in the presence of gallic acid and urea, over 100 cycles.

In some embodiments, the presence of urea, with or without ascorbate, in the detection solution was found to further reduce the amount of light-induced degradation of the nucleic acids when used with a polyphenolic compound. Table 2 and FIGS. 4 and 5, show this synergy in the presence of urea and ascorbate. While urea has a significant impact on reducing light-induced degradation when used in conjunction with a polyphenolic compound, using urea alone has only a minor impact with respect to any such protective benefits.

Methods of the invention that employ a detection solution having a polyphenolic compound protect the integrity of nucleic acids when they are exposed to repeated and/or intense irradiation, as might be employed in a variety of contexts, including without limitation, high throughput or rapid sequencing techniques such as, sequencing by synthesis and sequencing by ligation, nucleic acid microarray detection techniques such as gene chips and DNA microarrays, and quantitative polymerase chain reaction (Q-PCR) techniques such as real time polymerase chain reaction (PCR) and multiplex PCR. As described above, the presence of urea can enhance the protective role of the polyphenolic compound in any of these contexts. In the Examples disclosed herein, the use of the detection solution in sequencing by synthesis in an array format, in particular, lowered fluorescent signal decay and provided lower error rates over 50 to 120 cycles of repeated detection steps.

The detection solutions, which can be provided in kit form, can also be used in fluorescence detection techniques that have been employed in mechanistic biochemistry. For example, fluorescence polarization has been indicated as a powerful technique in studying molecular interactions, including without limitation, receptor-ligand interactions, such as hormone-receptor interactions, protein-peptide interactions, and DNA-protein interactions. For example, Singleton et al. *Tetrahedron* 63(17): (2007) incorporated a fluorescent guanine analog into oligonucleotides in studying RecA protein interactions with DNA. The detection solution employed in the methods disclosed herein can be used in real-time kinetic measurements where fluorophores are employed. The protective effects against light-induced degradation afforded by the detection solution need not be limited to the protection of nucleic acids. Thus, for example, the detection solution can also be used to protect the integrity of proteins, peptides, carbohydrates, and small molecules, any of which can be susceptible to reactive oxygen species, or the like, generated under conditions for measuring fluorescence emission.

As used herein, the term "nucleic acid" is intended to mean at least two nucleotides covalently linked together. Nucleic acid encompasses the term oligonucleotide, polynucleotide, and their grammatical equivalents. A nucleic acid of the present invention will generally contain phosphodiester bonds, although in some cases nucleic acid analogs can have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of labels, or to increase the stability and half-life of such molecules in physiological environments.

A nucleic acid of the present invention will generally contain a specific sequence of four nucleotide bases: adenine (A); cytosine (C); guanine (G); and thymine (T). Uracil (U) can also be present, for example, as a natural replacement for thymine when the nucleic acid is RNA. Uracil can also be used in DNA. A nucleic acid used in the invention can also include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. Exemplary non-native bases that can be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid of the invention can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil.

As used herein the term "array of nucleic acids" means a solid support having a plurality of spatially distinguishable nucleic acids disposed thereon or therein. The nucleic acids can be disposed in an ordered or random pattern of features. An individual feature can be, for example, a spatially isolated nucleic acid molecule, or an ensemble of nucleic acid molecules such as a cluster. An array can be a composite array comprising a plurality of individual arrays configured to allow processing of multiple samples. The individual arrays, referred to herein as "sub-arrays," include groups of nucleic acid features. Sub-arrays appear in distinct regions with in a larger array. The sub-arrays themselves can be ordered or non-ordered. Such sub-arrays can be optionally spatially addressable. Sub-arrays can include clusters of identical nucleic acids. An example of a composite array composed of individual sub-arrays is a microtiter plate having wells in which the plate as a whole is an array of nucleic acids (or composite array) while each individual well represents a sub-array within the larger composite array.

As used herein the term "nucleic acid member" means a single nucleic acid bound to a support that is part of an array and/or part of a sub-array within a composite array.

As used herein the term "support" refers to a substrate for immobilizing an array of nucleic acids. A "support" is a material having a rigid or semi-rigid surface to which a nucleic acid array can be attached or upon which nucleic acids can be synthesized and/or modified. Supports can include any resin, microbead, glass, controlled pore glass (CPG), polymer support, membrane, paper, plastic, plastic tube or tablet, plastic bead, glass bead, slide, ceramic, silicon chip, multi-well plate, nylon membrane, fiber optic, and PVDF membrane.

A support can include any flat wafer-like substrates and flat substrates having wells, such as a microtiter plate, including 96-well plates. Exemplary flat substrates include chips, slides, etched substrates, microtiter plates, and flow cell reactors, including multi-lane flow cell reactors having multiple microfluidic channels, such as the eight channel flow cell used in the cBot sequencing workstation (Illumina, Inc., San Diego, Calif.).

A support can also include beads, including magnetic beads, hollow beads, and solid beads. Beads can be used in conjunction with flat supports, such flat supports optionally also containing wells. Beads, or alternatively microspheres, refer generally to a small body made of a rigid or semi-rigid material. The body can have a shape characterized, for example, as a sphere, oval, microsphere, or other recognized particle shape whether having regular or irregular dimensions. The sizes of beads, in particular, include, without limitation, about 1 µm, about 2 µm, about 3 µm, about 5 µm, about 10 µm, about 20 µm, about 30 µm, about 40 µm, about 60 µm, about 100 µm, about 150 µm or about 200 µm in diameter. Other particles can be used in ways similar to those described herein for beads and microspheres.

The composition of a support can vary, depending for example, on the format, chemistry and/or method of attachment and/or on the method of nucleic acid synthesis. Support materials that can be used in accordance with the present disclosure include, but are not limited to, polypropylene, polyethylene, polybutylene, polyurethanes, nylon, metals, and other suitable materials. Exemplary compositions include supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "Microsphere Detection Guide" from Bangs Laboratories, Fishers Ind., which is incorporated herein by reference. A support particle can be made of cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, or TEFLON®. "Microsphere Detection Guide" from Bangs Laboratories, Fishers, Inc., hereby incorporated by reference in its entirety, is a helpful guide. Further exemplary supports within the scope of the present disclosure include, for example, those described in US Application Publication No. 02/0102578 and U.S. Pat. No. 6,429,027, both of which are incorporated herein by reference in their entirety.

As used herein the term "light-induced degradation" means the light-induced damage to one or more nucleic acids in an array of nucleic acids by exposure to illumination. Such degradation includes the complete or partial removal of individual nucleic acids from the support to which the array is attached. For example, light-induced degradation can include cleavage of the phosphodiester backbone at any of the nucleotides within an individual nucleic acid. Such degradation can also include removal of or reaction of a nucleic acid base or fluorescent tag causing a loss in hybridization or fluorescence function. Light-induced degradation can also include photo-induced cross-linking of nucleotides. The result of light-induced degradation can manifest as a decrease in fluorescence detection sensitivity in one or more regions or sub-arrays of an array nucleic acids when cycling through repeated detection steps, as might be observed, for example, when performing sequencing by synthesis, sequencing by ligation and microarray scanning. When used in conjunction with the term "inhibiting," this refers to a complete or partial block in the extent of damage, for example, as can be quantified by the observed strength of fluorescent emission. Light damage can be measured, for example, as a function of fluorescence signal intensity versus number of repeated irradiation (detection) steps performed on the array of nucleic acids. This process is sometimes referred to as T intensity decay. Another assessment of light damage can be measured as a function of error rate versus number of repeated irradiation (detection) steps performed on the array of nucleic acids.

As used herein the term "detection error rate" refers to a measure of the frequency of error in the identification of one or more fluorescently tagged nucleic acids in an array and/or sub-array of nucleic acids. For example, when measuring fluorescence in a scheme employing multi-color fluorescent tags, an error can arise by misidentification of a tagged sub-array when, for example, the signal-to-noise is eroded due to light-induced degradation of a plurality of nucleic acid members in the sub-array. Thus, the detection error rate is increased with the continual loss of individual nucleic acid members of an array or sub-array over numerous repeated cycles of irradiation.

As used herein the term "irradiating" refers to exposing an array of nucleic acids to illumination. The exposure can be for the purpose of fluorescence detection, for example. Irradiation can be performed with a laser or similar light source. Irradiation can be performed over a select section of the UV-visible spectrum and can employ one or more wavelength band filters. Irradiating can be performed over a period of time to collect sufficient fluorescent emission data. The term "intense" when used in reference to illumination refers to the amount of power that is employed during irradiation of a portion of an array of nucleic acids. Intense laser irradiation include an amount between about 5 milli-Watts to about 500 milliWatts and a powerdensity in an amount from between about 1 to about 200 W/mm$^2$.

As used herein the term "detection solution" means a solution containing compounds of the present invention that reduce light-induced degradation upon exposure of an array of nucleic acids to illumination. The detection solution is the solution that is used during a detection step employing irradiation.

As used herein the term "buffer," when used alone refers to any other buffer solution not used as a detection solution. Buffer solutions include those used in polymerase reactions, hybridizations, washing, or any other operation performed prior to the use of the detection solution employed in the invention.

As used herein the term "polyphenolic compound" refers to an aromatic compound having multiple hydroxyl groups (i.e. phenolic groups) on a benzene or other aromatic ring. The benzene, or other aromatic ring, can be optionally substituted with other substituents and/or fused rings. Exemplary polyphenolic compounds include, without limitation, gallic acid and lower alkyl esters thereof, monomethyl ethers thereof, and combinations of lower alkyl esters and monomethyl ethers thereof, pyrogallol, and hydroquinones, such as t-butyl hydroquinone (TBHQ), 2,4,5-trihydroxybutyrophenone (THBP).

As used herein the term "lower alkyl ester" refers to a C1-C6 alkyl chain ester of a carboxylic acid. In some embodiments, a "lower alkyl ester" refers to a C1-C4 alkyl chain ester of a carboxylic acid. Representative esters include methyl, ethyl, propyl, butyl, pentyl, and hexyl esters. Any of the forgoing esters can be optionally branched. Such branched esters include iso-propyl esters, sec-butyl esters, iso-butyl esters and tert-butyl esters, for example.

In some embodiments, the present invention provides a method of inhibiting light-induced degradation of nucleic acids during a detection step that includes irradiating the nucleic acids in the presence of a detection solution having a polyphenolic compound. The detection solution inhibits the amount of light-induced degradation of the nucleic acids.

In some embodiments, the present invention provides a method of detecting a nucleic acid having a fluorescent tag that includes a) irradiating the nucleic acid with light having a suitable wavelength to induce a fluorescence emission; b) detecting said fluorescence emission; and c) repeating steps a) and b). The irradiating step is carried out in the presence of a detection solution that includes a polyphenolic compound. The detection solution inhibits light-induced degradation of the nucleic acid. In some embodiments, the detection solution includes gallic acid, a lower alkyl ester thereof, or mixtures thereof. In still other embodiments, the detection solution includes a mixture of 1) gallic acid, a lower alkyl ester thereof, or mixtures thereof and 2) one or more compound(s) selected from urea, ascorbic acid or salt thereof, and isoascorbic acid or salt thereof.

Methods of the present invention include a detection solution for use during an irradiation step. The detection solution includes a polyphenolic compound which can be any aromatic system having two or more phenolic hydroxyl groups, any one of which can also be a lower alkyl ether. Polyphenolic compounds can belong to any number of structural classes such as lignans, tannins, gallocatechins, and flavanoids, such as flavonols, flavones, catechins, flavanones, anthocyanidins, and isoflavonoids. Polyphenolic compounds of the present invention can exist in a glycosylated form with one or more sugar residues attached to the polyphenolic compound. Such glycosylated forms can confer useful solubility properties in water, for example. Exemplary polyphenolic compounds include, without limitation, apigenin, astragalin, aurantinidin, azaleatin, butin, caffeic acid, catechin, cyanidin, epicatechin, epigallocatechin, gallocatechin, gallic acid and lower alkyl esters thereof, pyrogallol, delphinidin, ellagic acid, eriodictyol, homoeriodictyol, europinidin, fisetin, ferulic acid, galangin, genistein gossypetin, hesperitin, hesperidin, hydroquinones, such as p-hydroquinone, t-butyl hydroquinone (TBHQ), 2,4,5-trihydroxybutyrophenone (THBP), hydroxytyrosol, isorhamnetin, isosakuranetin, kaempferol, kaempferide, luteolin, luteolinidin, malvidin, myricetin, morin, naringenin, naringin, natsudaidain, pachypodol, pelargonidin, peonidin, petunidin, phloroglucinol, pinocembrin, poncirin, pterocarpans, pyrocatechol, quercetin, resorcinol, rhamnazin, rhamnetin, rosinidin, rutin, sinapyl alcohol, sakuranetin, sakuranin, sterubin, and tannic acid. In some embodiments, the polyphenolic compound can include gallic acid, a lower alkyl ester thereof, such as methyl gallate, ethyl gallate, propyl gallate, monomethyl ethers thereof, and combinations of lower alkyl esters and monomethyl ethers thereof, or mixtures thereof. When employing gallic acid, its derivatives, or mixtures thereof, this component of the detection solution can be present in a concentration ranging from between about 0.1 mM to about 200 mM.

Methods of the present invention employing a detection solution can further include one or more compounds to further reduce the amount of light-induced degradation. In some embodiments these secondary compounds can be selected from urea, ascorbic acid or salt thereof, and isoascorbic acid or salt thereof. Other secondary compounds that can be useful to reduce light-induced degradation include, without limitation, diethylhydroxylamine, diethyldithiocarbamate, 2-phenyl-5-benzimidazole sulfonic acid, and bis-(2,2,6,6-tetramethyl-4-piperidyl)sebacate. Such secondary agents can be present in a range of concentrations from between about 10 mM to about 5M, including 10 mM, 20 mM, 30 mM, 40 mM, 50 mM, 60 mM, 70 mM, 80 mM, 90 mM, 100 mM, 200 mM, 300 mM, 400 mM, 500 mM, 1M, 2M, 3M, 4M, and 5M, and any concentration in between.

In some embodiments, light-induced degradation can include oxidative damage, such as disclosed in Cooke et al. *FASEB J.* 17 (10): 1195-1214 (2003), which is incorporated herein by reference in its entirety. For example, light-induced degradation can include cleavage of the phosphodiester backbone at any of the nucleotides of a nucleic acid.

Other degradation pathways can include the formation of 8-oxo-2'-deoxyguanosine, the removal of or reaction of a nucleic acid base or fluorescent tag causing a loss in hybridization or fluorescence function, and the photo-induced cross-linking of nucleotides. Degradation by reactive oxygen radical species such as hydroxyl radical can damage nucleic acids by hydrogen atom abstraction processes, such as from the methyl group of thymine or from the C—H bonds of 2'-deoxyribose. Oxygen radical species can also oxidize nucleotides by reaction with unsaturations in nucleic acid bases, for example.

The detection solution having a polyphenolic compound can inhibit light-induced damage of nucleic acids by various mechanisms. Without being bound by theory, the polyphenolic compound can act as a more rapid fluorescence quencher of the excited fluorophore than oxygen, thus reducing or preventing the formation of singlet oxygen as indicated in Equation 1:

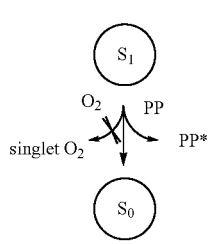

Equation 1

As indicated in equation 1, singlet state excited fluorophore $S_1$ can react preferentially with a polyphenolic compound (PP) in lieu of reaction with oxygen, to provide a return of the fluorophore to the singlet ground state $S_0$ while forming an excited state of the polyphenolic compound (PP*). One skilled in the art will recognize that the return to ground state $S_0$ can alternatively proceed via intersystem-crossing to a triplet excited state of the fluorophore $T_1$ (not shown). This non-radiative pathway to the triplet state of the fluorophore can be promoted by interaction with the polyphenolic compound. Ultimately, the energy transferred to the polyphenolic compound can be effectively dissipated.

Alternatively, any singlet oxygen generated by fluorescence quenching with oxygen can react with the polyphenolic compound to preserve the integrity of the nucleic acids. Similarly, any reactive oxygen species such as superoxide anion or hydroxyl radical formation formed via multiple photon absorption, as described above, can also be quenched by the polyphenolic compound present in the detection solution. Yet another possible mechanism by which the polyphenolic compound can reduce or prevent light-induced degradation is by intercepting and dissipating any high energy UV-visible radiation generated by multiple photon absorption by the fluorophore. In such a mechanism, the formation of reactive oxygen species and/or the indirect pyrimidine dimerization caused by high energy emission is reduced or prevented. Finally, one skilled in the art will appreciate that these high energy photochemical processes can operate in any combination.

As described above, inhibiting these light-induced degradation processes refers to a complete or partial blocking of the extent of damage, for example, as can be quantified by the observed strength of fluorescent emission with repeated exposure to intense illumination. Light-induce degradation can be measured, for example, as a function of fluorescence signal intensity versus number of repeated irradiation (detection) steps performed on the array of nucleic acids, such as in the sequencing by synthesis examples described herein below. This process is sometimes referred to as intensity decay. Another assessment of light-induced nucleic acid damage can be measured as a function of error rate versus number of repeated irradiation (detection) steps performed in an array of nucleic acids.

Still another assessment of light-induced damage can be to assay for nucleic acid degradation products. For example, measurement of 8-oxo-2'-deoxyguanosine is commonly used to assess oxidative damage to nucleic acids. Damage can also be assessed by quantifying the degree of thymine and cytosine homo- and heterodimerization. When employing detection methods on solid support, the inhibition of light-induced damage can be readily assessed by comparing arrays irradiated in the presence and absence of the detection solution and measuring a fluorescence signal intensity loss with repeated cycles of irradiation.

In some embodiments, methods of the present invention can be applied to nucleic acid detection in solution, while in other embodiments, methods of the invention can be applied to nucleic acids attached to a support, such as in an array format. When employing nucleic acids on a support, the nucleic acids can be present in ordered or non-ordered arrays. When using the detection solution having a polyphenolic compound, the amount of nucleic acids cleaved off a support can be reduced. Thus, in some embodiments, the light-induced degradation includes removal of a nucleic acid member from an array of nucleic acids.

When performing a detection step, irradiating the nucleic acids includes the use of an appropriate light source to excite a tag, such as a fluorescence tag. One skilled in the art will recognize that there are numerous tags available and that the conditions of the irradiation, such as choice of wavelength for irradiation and detection, will be guided by the choice of tags being employed in the nucleic acid detection process. The tags can be the same for each type of nucleotide, or each nucleotide type can have a unique tag. The tag is used in the identification of a particular incorporated of nucleotide within the nucleic acid. Thus, for example modified adenine, guanine, cytosine and thymine can all have attached a different fluorophore to allow them to be discriminated from one another readily. When sequencing on arrays, a mixture of tagged and untagged nucleotides can be used. Suitable tags include, but are not limited to, fluorescent tags, mass labels, magnetic labels and the like. By way of example, tags include biotin, dinitrophenol and fluorescein. Exemplary tagged nucleotides for use in the present methods are described in WO 04/018497, and U.S. Pat. Nos. 7,541,444 and 7,057,026, which are incorporated by reference herein in their entireties.

Detectable tags such as fluorophores can be linked to nucleotides via the nucleic acid base using a suitable linker. Suitable fluorophores include those described in WO 2007/135368, which is incorporated by reference herein in its entirety. The linker can be acid labile, photolabile or contain a disulfide linkage. Exemplary tags and linkages include those disclosed in WO03/048387. Other linkages, in particular phosphine-cleavable azide-containing linkers, can be employed in the invention as described in WO2004/018493.

Irradiation is carried out with an irradiation source which can include, for example, a laser or other source to generate sufficient excitation light intensity to produce detectable emission. The irradiation source can be used in conjunction with any combination of wavelength filters. The irradiation step can be pulsed in some embodiments, or continuous in other embodiments. The intensity of a light source can be in a range between about 5 milli Watts to about 500 milli Watts. The light source can be a high-energy short arc-discharge lamp for example. Exemplary discharge lamps include mercury burners, ranging in wattage from 50 to 200 Watts, and the xenon burners that range from 75 to 150 Watts, and LEDs. The exact choice of light source intensity can depend on the extinction coefficient of the fluorophore. Larger extinction coefficients indicate that the absorption of a photon, also referred to as quanta, at a given wavelength region is more likely. The quantum yield denotes the ratio of photons emitted to photons absorbed, and is usually a value between 0.1 and 1.0. The quantum yield is a measure of emission efficiency. Quantum yield values below 1 result from the loss of energy through non-radiative pathways, such as heat or a photochemical reaction, rather than fluorescence emission. Extinction coefficient, quantum yield, the intensity of the light source, and fluorescence lifetime are all important factors that contribute to the intensity and utility of fluorescence emission.

Methods of the invention can include an irradiation step conducted in a range from about 360 nm to about 800 nm, with a light source having power in a range between about 5 to about 500 m watts. As described above, between about 360 to about 800 nm, light-induced degradation can be ameliorated by the presence of the detection solution. This facilitates the use of multiple fluorophores for simultaneous fluorescent emission detection. Thus, method of the invention can be carried out while incorporating the four common bases with differential tags. The irradiation step can be conducted for a time period of about 0.1 seconds to about 10 minutes. 175-500 ms on GA, 2 mm/s scan speed. Such irradiation times can include pulsed or continuous irradiation.

When performing multiple steps incorporating differentially labeled nucleotides, methods of the invention can include replacing a solution with the detection solution prior to the irradiation step. For example, in sequencing by synthesis the solution used in adding the tagged nucleotide can be replaced with the detection solution prior to irradiation. In other embodiments, the detection solution can be used throughout each of the steps in sequencing by synthesis, including wash steps, in addition to the detection step.

Fluorescent light emitted from the fluorophore can be detected at the appropriate wavelength using a suitable detection system such as, for example, a Charge-Coupled-Device (CCD) camera, which can optionally be coupled to a magnifying device, a fluorescent imager or a confocal microscope. An alternate suitable detection system employs a complementary metal-oxide-semiconductor (CMOS) detector. If sequencing is carried out on an array, detection of an incorporated base can be carried out by using a confocal scanning microscope to scan the surface of the array with a laser, to image fluorescent labels attached to the incorporated nucleotides. Alternatively, a sensitive 2-D detector, such as a charge-coupled detector (CCD), can be used to visualize the signals generated. This technique is particularly useful with single molecule arrays. Other techniques such as scanning near-field optical microscopy (SNOM) are available and can be used when imaging dense arrays. For a description of scanning near-field optical microscopy, see Moyer et al., Laser Focus World 29:10, 1993. An additional technique that can be used is surface-specific total internal reflection fluorescence microscopy (TIRFM); see, for example, Vale et al., Nature, (1996) 380: 451-453).

When employing detection solutions of the invention to sequencing by synthesis, for example, the method can include adding an additional fluorescently tagged nucleotide to the array and repeating the detection steps each cycle. Methods of the invention employing repeated nucleotide addition and detection steps can include at least 25 cycles in some embodiments, at least 75 cycles in other embodiments, and at least 100 cycles in yet other embodiments. Methods of the invention include repeating adding and detection steps for a number of cycles in a range from between about 100 cycles to about 1,000 cycles, in some embodiments, from between about 100 cycles to about 500 cycles, in other embodiments, and from between about 100 cycles to about 300 cycles, in yet other embodiments.

The ability to accurately sequence 25 or more, 50 or more, 75 or more, or 100 or more consecutive nucleotides in a sequencing reaction is a significant advantage in applications such as genome re-alignment.

In some embodiments, an array of nucleic acids includes a primer template. Nucleic acid "sequencing-by-synthesis" involves sequential addition of one or more nucleotides to a growing polynucleotide chain in the 5' to 3' direction using a polymerase in order to form an extended polynucleotide chain complementary to a template nucleic acid to be sequenced. Exemplary sequencing methods are described, for example, in Bentley et al., Nature 456:53-59 (2008), WO 04/018497; U.S. Pat. No. 7,057,026; WO 91/06678; WO 07/123744; U.S. Pat. No. 7,329,492; U.S. Pat. No. 7,211, 414; U.S. Pat. No. 7,315,019; U.S. Pat. No. 7,405,281, and US 2008/0108082, each of which is incorporated herein by reference. The identity of the base present in one or more of the added nucleotide (s) is determined in the detection step. The identity of the added base can be determined after each nucleotide incorporation step. The sequence of the template can then be inferred using conventional Watson-Crick base-pairing rules. For the avoidance of doubt "sequencing" can also encompass incorporation and identification of a single nucleotide. Determination of the identity of a single base can be useful, for example, in the scoring of single nucleotide polymorphisms.

The nucleic acid template for a sequencing reaction can include a double-stranded region having a free 3' hydroxyl group which serves as a primer or initiation point for the addition of further nucleotides in the sequencing reaction. The region of the template to be sequenced will overhang this free 3' hydroxyl group on the complementary strand. The primer bearing the free 3' hydroxyl group can be added as a separate component (e.g. a conventional oligonucleotide sequencing primer) which hybridizes to a region of the template to be sequenced. Alternatively, the primer and the template strand to be sequenced can each form part of a partially self-complementary nucleic acid strand capable of forming an intramolecular duplex, such as for example a hairpin loop structure. Nucleotides are added successively to the free 3' hydroxyl group, resulting in synthesis of a polynucleotide chain in the 5' to 3' direction. After each nucleotide addition the nature of the base which has been added can be determined, thus providing sequence information for the nucleic acid template.

Incorporation of a nucleotide into a nucleic acid strand (or polynucleotide) refers to joining of the nucleotide to the free 3' hydroxyl group of the nucleic acid strand via formation of a phosphodiester linkage with the 5' phosphate group of the nucleotide. The nucleic acid template to be sequenced can be DNA or RNA, or even a hybrid molecule that includes both deoxynucleotides and ribonucleotides. The nucleic acid can include naturally occurring and/or non-naturally occurring nucleotides and natural or non-natural backbone linkages.

Nucleic acid templates to be sequenced can be attached to a solid support via any suitable linkage method known in the art. Linkage can be via covalent attachment, for example. If the templates are "arrayed" on a solid support then the array can take any convenient form. Thus, the method of the invention is applicable to all types of "high density" arrays, including single-molecule arrays and clustered arrays.

In some embodiments, the detection solution reduces a detection error rate, when sequencing, by greater than 20% relative to a control lacking the polyphenolic compound. The detection error rate is further reduced in the presence of one or more compound(s) selected from urea, ascorbic acid or salt thereof, and isoascorbic acid or salt thereof in the detection solution. In further embodiments, the detection solution reduces a detection error rate by greater than 40% relative to a control lacking the polyphenolic compound, which error rate is also enhanced by the presence of one or more compound(s) selected from urea, ascorbic acid or salt thereof, and isoascorbic acid or salt thereof. In still further embodiments, the detection solution reduces a detection error rate by greater than 50% relative to a control lacking the polyphenolic compound.

Error rates can be determined, for example, as described in Bentley, et al., "Accurate whole human genome sequencing using reversible terminator chemistry" *Nature* 456:53-59 (2008). The error rate is the sequencing error per cycle as determined by alignment of the phiX sequence against a phiX standard genome using the ELAND algorithm that is part of the standard pipeline analysis as described in the Pipeline User Guide (Illumina, Inc., San Diego, Calif.) and Bentley et al., *Nature* 456:53-59 (2008).

In some embodiments, the present invention provides a method of inhibiting light-induced degradation of nucleic acids during a detection step that includes irradiating a portion of the nucleic acids in the presence of a detection solution that includes gallic acid, a lower alkyl ester thereof, or mixtures thereof. The detection solution reduces the amount of light-induced degradation of the nucleic acids. The use of gallic acid and its derivatives are shown below in Examples I and II. Gallic acid in its free form is capable of ionizing to carboxylate and its effectiveness as an inhibitor of light-induced degradation can therefore be dependent on the pH of the system. By comparison, lower gallate esters can demonstrate a relatively constant effectiveness over a range of pHs.

Without being bound by theory, one skilled in the art will recognize that a carboxylic acid group is modestly more electron withdrawing than an ester. Thus, if gallic acid and related compounds are serving in an antioxidant role, one might expect an ester to perform slightly better than a carboxylic acid in reducing light-induced degradation. However, this benefit of gallate esters can be ameliorated by the need for water solubility of the ester. In this regard, the ionizable carboxylic acid is useful to confer water solubility. As such, in some embodiments, detection solutions of the present invention provide gallic acid, lower alkyl esters of gallic acid, or mixtures thereof.

One skilled in the art will also recognize that other ester derivatives of gallic acid can be useful in the invention where sufficient water solubility is conferred to the gallate ester. In some embodiments, additional solubility can be realized by use of a small amount of a co-solvent such as dimethyl sulfoxide (DMSO). By employing such co-solvents in small quantities, the use of any gallate ester can be effective in reducing light-induced degradation of nucleic acids. In some embodiments, a water solublizing ester group can be employed, such as a PEG ester of gallic acid. In such embodiments, the gallate ester can benefit from the improved antioxidant activity of an ester over a carboxylic acid, without sacrificing the useful water solubility of the carboxylic acid functional group.

In yet further embodiments, the present invention provides a method of inhibiting light-induced degradation of nucleic acids during a detection step that includes the nucleic acids in the presence of a detection solution that includes 1) gallic acid, a lower alkyl ester thereof, or mixtures thereof, and 2) one or more compound(s) selected from urea, ascorbic acid or salt thereof, and isoascorbic acid or salt thereof. This detection solution reduces the amount of light-induced degradation of the nucleic acids. As demonstrated in Examples I and II, urea has shown a synergism in reducing light-induced degradation of nucleic acids. Unsubstituted urea, $(NH_2)_2CO$, is not generally classified as an antioxidant, and thus the role of urea in providing a synergistic effect in reducing light-induced degradation is not readily attributable to antioxidant activity. For example, it has been indicated that urea affords no apparent protection against reactive oxygen species at physiological concentrations (Glazer, *FASEB J.* 2:2487-2491 (1988)). Moreover, it has been indicated that urea affords no apparent protection against reaction with singlet oxygen (Dahl et al. Photochem. Photobiol. 47(3):357-362 (1988)). Urea absorbs in the UV-visible region substantially only below 245 nm. In this region of the UV spectrum pyrimidine dimerization is a significant pathway with respect to light-induced nucleic acid damage. However, the role of urea in providing additional protection against light-induced damage under the conditions of fluorescence detection, as provided in the Examples, are not yet fully understood.

In some embodiments, the present invention is directed to a kit for use in accordance with the aforementioned methods. The kit generally includes one or more nucleotides, an enzyme capable of catalyzing incorporation of the nucleotides into a nucleic acid strand complementary to a nucleic acid template to be sequenced, and a polyphenolic compound suitable for preparing a detection solution. The polyphenolic compound can include gallic acid, a lower alkyl ester thereof, or mixtures thereof. In some embodiments, the kit further includes a secondary compound selected from urea, ascorbic acid or salt thereof, and isoascorbic acid or salt thereof. The kit can further include buffer salts and a set of instructions for carrying out preparation of a solution for use in fluorescence experiments.

Embodiments described herein can be used in a variety of known methods and/or compositions for detecting nucleic acids, wherein light-induced degradation of nucleic acids occurs or is suspected to occur. For example, the methods and compositions described herein are particularly useful when a detection method requires repeated or prolonged exposure of nucleic acids to light. In particular, detection of fluorescently tagged nucleic acids is often used by irradiating a sample with light that has a suitable wavelength to induce a fluorescent emission from a nucleic acids that contains a fluorescent tag. During the irradiation steps of these methods, as described herein, damage to the nucleic acids can occur. The repeated or prolonged exposure can result in a decrease in fluorescence detection sensitivity, which can manifest, for example, as an increase in detection error rates and reduced signal-to-noise ratios. Non-limiting examples of methods wherein the methods and/or compositions for detecting nucleic acids that have repeated or prolonged exposure to light include high throughput or rapid sequencing techniques such as, sequencing by synthesis and sequencing by ligation, nucleic acid microarray detection techniques such as, gene chips and DNA microarrays, and quantitative polymerase chain reaction (Q-PCR) techniques such as, real time polymerase chain reaction (PCR) and multiplex PCR.

One useful method for high throughput or rapid sequencing is sequencing by synthesis (SBS). SBS techniques that require repeated or prolonged irradiation of nucleic acids with light include, but are not limited to, the Genome Analyzer systems (Illumina Inc., San Diego, Calif.) and the True Single Molecule Sequencing (tSMS)™ systems (Helicos BioSciences Corporation, Cambridge, Mass.). Briefly, a number of sequencing by synthesis reactions are used to elucidate the identity of a plurality of bases at target positions within a target sequence. All of these reactions rely on the use of a target nucleic acid sequence having at least two domains; a first domain to which a sequencing primer will hybridize, and an adjacent second domain, for which sequence information is desired. Upon formation of an assay complex, extension enzymes are used to add dNTPs to a sequencing primer that is hybridized to first domain, and each addition of dNTPs is read to determine the identity of the added dNTP. This may proceed for many cycles. SBS techniques such as, the Genome Analyzer systems (Illumina Inc., San Diego, Calif.) and the True Single Molecule Sequencing (tSMS)™ systems (Helicos BioSciences Corporation, Cambridge, Mass.), utilize labeled nucleotides to determine the sequence of a target nucleic acid molecule. A target nucleic acid molecule can be hybridized with a primer and incubated in the presence of a polymerase and a labeled nucleotide containing a blocking group. The primer is extended such that the nucleotide is incorporated. The presence of the blocking group permits only one round of incorporation, that is, the incorporation of a single nucleotide. The presence of the label permits identification of the incorporated nucleotide. A plurality of homogenous single nucleotide bases can be added during each cycle, such as used in the True Single Molecule Sequencing (tSMS)™ systems (Helicos BioSciences Corporation, Cambridge, Mass.) or, alternatively, all four nucleotide bases can be added during each cycle simultaneously, such as used in the Genome Analyzer systems (Illumina Inc., San Diego, Calif.), particularly when each base is associated with a distinguishable label. After identifying the incorporated nucleotide by its corresponding label, both the label and the blocking group can be removed, thereby allowing a subsequent round of incorporation and identification. Determining the identity of the added nucleotide base includes repeated exposure of the newly added labeled bases a light source that can induce a detectable emission due the addition of a specific nucleotide base, i.e. dATP, dCTP, dGTP or dTTP. The methods and compositions disclosed herein are particularly useful for such SBS techniques.

Another useful method for high throughput or rapid sequencing technique is sequencing by ligation. Sequencing by ligation is a well known method for sequencing that requires repeated or prolonged irradiation of di-base probes with light. Exemplary systems that use sequencing by synthesis include the SOLiD™ system by Applied Biosystems (Life Technologies, Carlsbad, Calif.). Briefly, methods for sequencing by ligation include hybridizing sequencing primers to adapter sequences immobilized to templated beads. A set of four fluorescently labeled di-base probes compete for ligation to the sequencing primer. Specificity of the di-base probe is achieved by interrogating every 1st and 2nd base in each ligation reaction. Following a series of ligation cycles, the extension product is removed and the template is reset with a sequencing primer complementary to the n–1 position for a second round of ligation cycles. Multiple cycles of ligation, detection and cleavage are performed with the number of cycles determining the eventual read length. Sequencing by ligation methods have been developed by Applied Biosystems in its Agencourt platform (see Ronaghi et al., *Science* 281:363 (1998); Dressman et al., *Proc. Natl. Acad. Sci. USA* 100:8817-8822 (2003); Mitra et al., *Proc. Natl. Acad. Sci. USA* 100:55926-5931 (2003)).

In addition, the methods and compositions described herein can be particularly useful for sequencing from an array of nucleic acids, where multiple sequences can be read simultaneously from multiple positions on the array since each nucleotide at each position can be identified based on its identifiable label. Exemplary methods are described in US 2009/0088327; US 2010/0028885; and US 2009/0325172, each of which is incorporated herein by reference.

Other methods know in the art where repeated or prolonged irradiation of nucleic acids with light include nucleic acid microarray detection techniques, such as gene chips and DNA microarrays. It is well know in the art that reliability and consistency problems exist when scanning nucleic acid microarrays, particularly when scanning the same microarray more than once. However, multiple scans can be required in order to obtain the full dynamic range of the labeled nucleic acids, for example, when using a microarray to determine gene expression levels. A single scan attempts to capture the whole range of expression in the given samples. This may not give the true picture of the expression of the whole set of genes when a wide range of expression is present. For example, a gene in the sample may express as few as 200 copies, whereas a separate gene in the same sample may express 50,000 copies. In this aspect, the methods and compositions described herein are particularly useful in maintaining the integrity of the nucleic acids over multiple scans.

Examples of nucleic acid microarray detection techniques known in the art include, but are not limited to, LabCard (ACLARA Bio Sciences Inc., Santa Clara, Calif.); GeneChip (Affymetrix, Inc, Santa Clara, Calif.); LabChip (Caliper Technologies Corp, Hopkinton, Mass.); microarrays produced by SurePrint technology (Agilent Technologies, Santa Clara, Calif.); a low-density array with electrochemical sensing (Clinical Micro Sensors Inc., Pasadena, Calif.); LabCD System (Tecan Trading AG, Zurich, Switzerland.); Omni Grid (Gene Machines, Stillwater, Okla.); Q Array (Genetix Ltd., Boston, Mass.); a high-throughput, automated mass spectrometry systems with liquid-phase expression technology (GeneTrace Systems, Inc., Menlo Park, Calif.); a thermal jet spotting system (Hewlett Packard Company; Palo Alto, Calif.); Hyseq HyChip (Hyseq, Inc., Sunnyvale, Calif.); BeadArray (Illumina, Inc., San Diego, Calif.); GEM (Incyte Microarray Systems, Fremont, Calif.); a high-throughput microarrying system that can dispense from 12 to 64 spots onto multiple glass slides (Intelligent Bio-Instruments, Waltham, Mass.); Molecular Biology Workstation and NanoChip (Nanogen, Inc., San Diego, Calif.); a micro fluidic glass chip (Orchid Cellmark, Inc., Dayton, Ohio); BioChip Arrayer with four PiezoTip piezoelectric drop-on-demand tips (Packard Instruments, Inc., Meriden, Conn.)); FlexJet (Rosetta Inpharmatic, Inc., Kirkland, Wash.); MALDI-TOF mass spectrometer (Sequenome, San Diego, Calif.); ChipMaker 2 and ChipMaker 3 (Arrayit Corporation, Sunnyvale, Calif.); and GenoSensor (Abbot Molecular, Des Plaines, Ill.) as identified and described in Heller, *Annu Rev. Biomed. Eng.* 4:129-153 (2002). Examples of gene chips or a microarrays are also described in U.S. Patent Publ. Nos.: 2007-0111322, 2007-0099198, 2007-0084997, 2007-0059769 and 2007-0059765 and U.S. Pat. Nos. 7,138,506, 7,070,740, and 6,989,267.

Quantitative polymerase chain reaction (Q-PCR) techniques such as, real time polymerase chain reaction (PCR) and multiplex PCR are well known methods of characterizing and quantifying nucleic acids. Such techniques require repeated or prolonged exposure of nucleic acids to light, wherein the methods and compositions described herein are useful for inhibiting light-induce degradation. Five of the most popular chemistries for performing real-time PCR and/or multiplex PCR include TaqMan® (Life Technologies, Carlsbad, Calif.), Molecular Beacons, FRET probes, Scorpions® (Sigma-Aldrich, Inc, St. Louis, Mo.) and SYBR® Green (Life Technologies, Carlsbad, Calif.). All of these chemistries allow detection of PCR products via the generation of a fluorescent signal. TaqMan® probes, Molecular Beacons, FRET probes and Scorpions® depend on Förster Resonance Energy Transfer (FRET) to generate the fluorescence signal via the coupling of a fluorogenic dye molecule and a quencher moiety to the same or different oligonucleotide substrates. SYBR® Green is a fluorogenic dye that exhibits little fluorescence when in solution, but emits a strong fluorescent signal upon binding to double-stranded DNA.

TaqMan® probes depend on the 5'-nuclease activity of the DNA polymerase used for PCR to hydrolyze an oligonucleotide that is hybridized to the target amplicon. TaqMan® probes are dual labeled oligonucleotides that have a fluorescent reporter dye attached to the 5' end and a quencher moiety coupled to the 3' end. Typically, TaqMan® probes consist of a 18-22 bp oligonucleotide probe. These probes are designed to hybridize to an internal region of a PCR product. In the unhybridized state, the proximity of the fluorescent reporter dye and the quench molecules prevents the detection of fluorescent signal from the probe. When conducting a real time PCR experiment, a TaqMan® probe, complementary to the target sequence is added to the PCR reaction mixture. During PCR, the probe anneals specifically between the forward and reverse primer to an internal region of the PCR product. When the polymerase replicates a template on which a TaqMan® probe is bound, the 5'-nuclease activity of the polymerase cleaves the probe. This decouples the fluorescent and quenching dyes and FRET no longer occurs. Thus, fluorescence increases in each cycle, proportional to the amount of probe cleavage.

Like TaqMan® probes, Molecular Beacons also use FRET to detect and quantitate the synthesized PCR product via a fluorophore coupled to the 5' end and a quench attached to the 3' end of an oligonucleotide substrate. A Molecular Beacon consists of 4 parts, namely a loop, stem, a 5' fluorophore and a 3' quencher. The loop is typically a 18-30 base pair region of the molecular beacon which is complementary to the target sequence. The stem sequence lies on both ends of the loop and is typically 5-7 bp long. Both the stem sequences are complementary to each other. The 5' end of the Molecular Beacon contains a fluorophore and the 3' end of the molecular beacon contains a quencher dye that when the beacon is in a closed loop shape, prevents the fluorophore from emitting light. When a Molecular Beacon hybridizes to a target, the fluorescent dye and quencher are separated, FRET does not occur, and the fluorescent dye emits light upon irradiation. However, unlike TaqMan probes, Molecular Beacons are designed to remain intact during the amplification reaction, and must rebind to the target in every cycle for signal measurement. Molecular beacons can report the presence of specific nucleic acids from a homogeneous solution. For quantitative PCR, molecular beacons bind to the amplified target following each cycle of amplification and the resulting signal is proportional to the amount of template.

FRET probes are a pair of fluorescent probes designed to hybridize to adjacent regions on the target DNA as described by Didenko, *Biotechniques* 31(5):1106-1121 (2001). Fluorophores are so chosen that the emission spectrum of one overlaps significantly with the excitation spectrum of the other. During PCR, the two different oligonucleotides hybridize to adjacent regions of the target DNA such that the fluorophores, which are coupled to the oligonucleotides, are in close proximity in the hybrid structure. The donor fluorophore is excited by an external light source, then passes part of its excitation energy to the adjacent acceptor fluorophore. The excited acceptor fluorophore emits light at a different wavelength which can then be detected in specific channels and measured. The light source cannot excite the acceptor dye.

With Scorpion® probes, sequence-specific priming and PCR product detection is achieved using a single oligonucleotide as described in Bates et al., *Molecular Plant Pathology* 2(5):275-280 (2001); Hart et al., *J. Clin. Microbiol.* 39(9): 3204-12 (2001), and Thelwell et al., *Nucleic Acids Research* 28(19):3752-61 (2000). Scorpion® primers are bi-functional molecules in which a primer is covalently linked to the probe. The Scorpion® probe maintains a stem-loop configuration in the unhybridized state. A fluorophore is attached to the 5' end and is quenched by a moiety coupled to the 3' end. The 3' portion of the stem also contains sequence that is complementary to the extension product of the primer. This sequence is linked to the 5' end of a specific primer via a non-amplifiable monomer. In the absence of the target, the quencher nearly absorbs the fluorescence emitted by the fluorophore. In the initial PCR cycles, the primer hybridizes to the target and extension occurs due to the action of polymerase. After extension of the Scorpion® primer, the specific probe sequence is able to bind to its complement within the extended amplicon thus opening up the hairpin loop and separating the fluorophore and the quencher, which leads to an increase in fluorescence emitted. The fluorescence can be detected and measured in the reaction tube during each successive cycle of amplification.

SYBR® Green provides one of the simplest and most economical format for detecting and quantitating PCR products in real-time reactions. SYBR® Green is an asymmetrical cyanine dye as described by Zipper et al., *Nucleic Acids Res.* 32(12):e103 (2004). SYBR® Green preferentially binds double-stranded DNA, but will stain single-stranded DNA with lower performance. The resulting DNA-dye-complex absorbs blue light ($\lambda$max=488 nm) and emits green light ($\lambda$max=522 nm). Since the dye preferentially binds to double-stranded DNA, there is no need to design a probe for any particular target being analyzed. However, detection by SYBR Green requires extensive optimization. Since the dye cannot distinguish between specific and non-specific product accumulated during PCR, as any PCR product accumulates, fluorescence increases. The advantages of SYBR® Green are that it is inexpensive, easy to use, and sensitive. The disadvantage is that SYBR® Green will bind to any double-stranded DNA in the reaction, including primer-dimers and other non-specific reaction products, which results in an overestimation of the target concentration. For single PCR product reactions with well designed primers, SYBR® Green can work extremely well, with spurious non-specific background only showing up in very late cycles. Similar cyanine dyes are known in the art and include SYBR® Green II, SYBR Gold, YO (Oxazole Yellow), TO (Thiazole Orange), and PG (PicoGreen).

TaqMan® probes, Molecular Beacons and Scorpions® allow multiple DNA species to be measured in the same sample, also known as multiplex PCR, since fluorescent dyes with different emission spectra may be attached to the different probes. Multiplex PCR allows internal controls to be co-amplified and permits allele discrimination in single-tube, homogeneous assays. These hybridization probes afford a level of discrimination impossible to obtain with SYBR Green, since they will only hybridize to true targets in a PCR and not to primer-dimers or other spurious products. However, multiplex PCR will also require additional repeated and prolonged irradiation steps in order quantitate the multiple fluorescent emissions from a single sample. Accordingly, the methods and compositions described herein are useful for inhibiting light-induced nucleic acid degradation.

It is understood that modifications which do not substantially affect the activity of the various embodiments of this invention are also provided within the definition of the invention provided herein. Accordingly, the following examples are intended to illustrate but not limit the present invention.

Example I

Error Rate and 20 Cycle Intensity

This Example shows error rates with repeated detection cycles in a sequencing by synthesis format using an eight lane flowcell. The data in this example was generated using the standard procedure of setting up a sequencing run on HiSeq instruments (Illumina Inc., San Diego, Calif.) according to the HiSeq UserGuide and using standard Illumina Sequencing reagents, except for the detection solution. Methods for the standard protocols are available from Illumina, Inc. and referenced in Bentley et al., Nature 456:53-59 (2008), which is incorporated by reference herein in its entirety. Briefly, a plurality of fluorescently labeled modified nucleotides is used to sequence clusters of amplified DNA present on the surface of a flow cell. To initiate the first sequencing cycle, one or more differently labeled nucleotides, and appropriate reagents, e.g., DNA polymerase, etc., are flowed into/through the flow cell by a fluid flow system. After incorporation, non-incorporated nucleotides are washed away by flowing a wash solution through the flow cell. A detection solution is then flowed through the flow cell while lasers are used to excite the nucleic acids and induce fluorescence. A deblocking reagent is then added to the flow cell to remove reversible terminator groups from the DNA strands that were extended and detected. The deblocking reagent is then washed away by flowing a wash solution through the flow cell. The flow cell is then ready for a further cycle of sequencing starting with introduction of a labeled nucleotide as set forth above. The fluidic and detection steps are repeated several times to complete a sequencing run.

To generate the detection solution used in the experiments, the test compounds were added from powder to the detection solution to the indicated final solutions in Table 1 and the pH was checked and adjusted if needed. The "Image Cycle Pump" feature was used to test 3 compounds per run such that lanes 1 and 2 were scanned in control detection solution, lanes 3 and 4 in detection solution containing a first test compound, lanes 5 and 6 in detection solution containing a second test compound and lanes 7 and 8 in detection solution containing a third test compound. The intensity decay and error rates were compared between the lanes that received control detection solution and those that received detection solution containing the test compounds.

Example II

Error Over Cluster PF

This Example shows a gallic acid dose response using 20 (lanes 3 and 4) 40 (lanes 5 and 6) and 80 mM (lanes 7 and 8) with lanes 1 and 2 being the no gallic acid controls.

Figure 3:
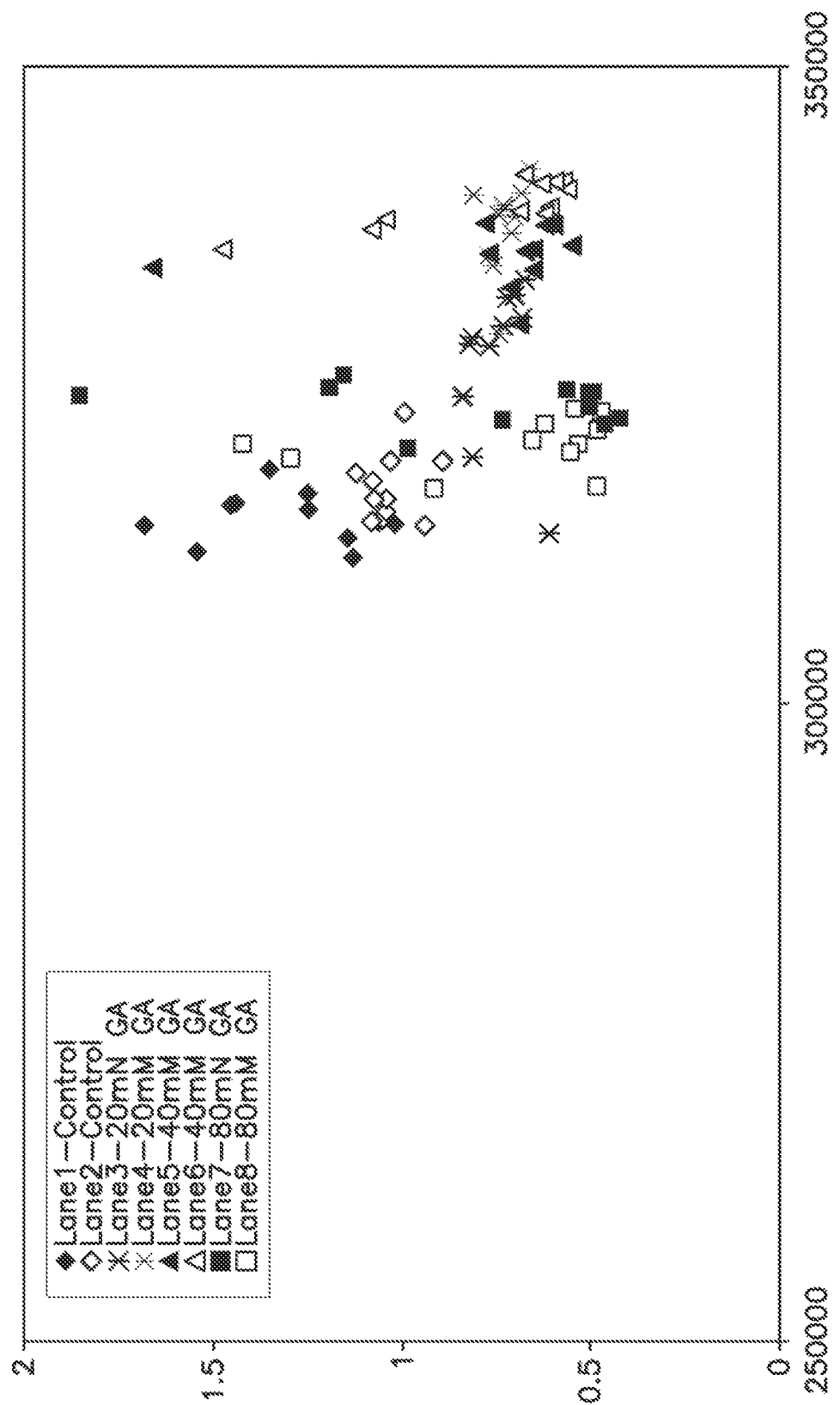
FIG. 3 shows a graph plotting error versus cluster passing filter (PF) number.

This experiment was carried out exactly as described above in Example I. FIG. 3 shows a graph plotting error versus cluster passing filter (PF) number. The graph in FIG. 3 shows a significant dose-dependent improvement in error rates (y axis) for all gallic acid concentrations. The graphs also shows an improvement in clusters passing filters with an optimum of 40 mM—at 80 mM the number of clusters passing filter is reduced compared to 40 mM.

Example III

Coverage Plots

This Example shows the errors per position in a reference sequence.

This experiment was carried out exactly as described in Example I. FIG. 4 shows coverage plots for a control sequence, in the presence of gallic acid, in the presence of urea, and in the presence of gallic acid and urea, over 75 cycles. FIG. 5 shows coverage plots for a control sequence, in the presence of gallic acid, in the presence of urea, and in the presence of gallic acid and urea, over 100 cycles. Coverage plots analyze error (Y axis) per position in a given genome (x axis, using phiX genome as standard). The data shows that the phiX genome contains hot-spots with significantly higher error rate than the rest of the genome. Gallic acid in the detection solution reduces the error rate certain hot spot significantly while not affecting other hot spot as much. Urea by itself has very little effecting reducing the error rates but show a remarkable synergy with gallic acid that almost eliminates the error in most hotspots and even lowers the error of the dominant hot spot (around position 4300) while each of the compounds alone have no effect.

TABLE 1

| Entry number | Compound | Concentration mM | Error Rate | cycle20 Int |
|---|---|---|---|---|
| 1 | 1,4-Dihydroxy-2,6-dimethoxybenzene | 10 | 0.81 | 73.91 |
| 2 | 1,4-Dihydroxy-2-Naphthoic Acid | 10 | 5.22 | 64.32 |
| 3 | 2,2,6,6-Tetramethyl-4-piperidinol | 10 | 3.11 | 50.47 |
| 4 | 2,3 Dihydroxy Benzoic Acid | 50 | 0.63 | 78.86 |
| 5 | 3,5 Dihydroxy Benzoic Acid | 10 | 0.62 | 75.66 |
| 6 | 3,4 Dihydroxy Benzoic Acid | 10 | 0.73 | 78.60 |
| 7 | 2-Phenyl-5-benzimidazole sulfonic acid | 30 | 0.97 | 79.28 |
| 8 | 3,4,5-Trihydroxybenzamide | 10 | 2.08 | 76.71 |
| 9 | 3,4-Diaminobenzoic acid | 10 | 2.01 | 80.47 |
| 10 | 3-Aminobenzoic Acid | 10 | 0.33 | 75.59 |
| 11 | 3-Amino-4-Hydroxybenzoic Acid | 10 | 1.66 | 80.72 |
| 12 | 3-Hydroxybenzoic Acid | 10 | 2.23 | 70.79 |
| 13 | 3-Hydroxy-4-Nitrobenzoic Acid | 10 | 3.72 | 73.50 |
| 14 | 3-Hydroxyanthranilic Acid | 10 | 0.85 | 81.59 |
| 15 | 3-HydroxyCinnamic Acid | 10 | 1.49 | 76.84 |
| 16 | 4-Aminosalicylic Acid | 10 | 1.75 | 80.08 |
| 17 | 4-Amino Benzoic Acid | 10 | 0.57 | 74.85 |
| 18 | 4-Amino3-Hydroxybenzoic Acid | 10 | 1.61 | 79.21 |

TABLE 1-continued

| Entry number | Compound | Concentration mM | Error Rate | cycle20 Int |
|---|---|---|---|---|
| 19 | 4-Amino-3-Methoxybenzoic acid | 10 | 2.36 | 74.98 |
| 20 | 4-Hydroxybenzoic Acid | 10 | 2.01 | 74.76 |
| 21 | 4-Hydroxy-3-Nitrobenzoic acid | 10 | 3.09 | 75.91 |
| 22 | 4-Hydroxycinnamic Acid | 10 | 1.92 | 68.78 |
| 23 | 5-benzoyl-4-hydroxy-2-methoxy benzene sulfonic acid | 10 | 2.58 | 75.53 |
| 24 | 1-Aza-3,7-dioxabucyclo{3,3,0]-octane-5-methanol | 30 | 0.38 | 78.19 |
| 25 | Benzoic Acid | 100 | 2.24 | 71.98 |
| 26 | Bis [2,2,6,6-Tetramethyl-4-piperidone] sebacate | 20 | 0.92 | 76.17 |
| 27 | Caffeic Acid | 10 | 0.41 | 76.60 |
| 28 | Catechol | 10 | 1.58 | 78.54 |
| 29 | Chlorogenic Acid | 10 | 0.86 | 79.65 |
| 30 | 1,4-Diazabicyclo[2,2,2]octane | 10 | 1.02 | 76.32 |
| 31 | Diaminotoluene sulfate | 10 | 0.56 | 76.08 |
| 32 | Diethyldithiocarbamate | 25 | 1.39 | 76.28 |
| 33 | N,N-Diethylhydroxylamine | 30 | 0.43 | 78.94 |
| 34 | Diethyldithiocarbamate | 10 | 1.46 | 79.30 |
| 35 | N,N-Diethylhydroxylamine | 10 | 1.41 | 76.66 |
| 36 | 1,4-Dimethylpiperazine | 10 | 1.03 | 76.17 |
| 37 | Diethylenetriaminepentaacetic acid | 10 | 1.28 | 68.53 |
| 38 | 5-Ethoxysalicylic acid | 10 | 0.50 | 75.31 |
| 39 | Ethylgallate | 10 | 0.36 | 85.89 |
| 40 | Ferulic Acid | 10 | 0.77 | 72.58 |
| 41 | Gallic Acid | 100 | 1.39 | 87.37 |
| 42 | Gallic acid | 200 | 0.82 | 78.83 |
| 43 | Gallic acid | 20 | 0.58 | 84.30 |
| 44 | Gallic Acid | 50 | 0.39 | 84.98 |
| 45 | Glutathione | 10 | 0.75 | 74.70 |
| 46 | Histidine | 10 | 0.92 | 76.18 |
| 47 | 5-methoxysalicylic acid | 10 | 0.76 | 73.57 |
| 48 | Hesperidin methyl chalcone | 30 | 0.26 | 79.84 |
| 49 | Hydrazine | 10 | 0.63 | 75.32 |
| 50 | Hydroquinone | 10 | 0.92 | 79.48 |
| 51 | Laurylgallate | 10 | 1.69 | 65.94 |
| 52 | α-Lipoic acid | 10 | 1.01 | 76.32 |
| 53 | β-Mercaptoethylamine hydrochloride | 10 | 1.75 | 72.29 |
| 54 | Melatonin | 1 | 0.43 | 72.42 |
| 55 | Methyl 3,4,5-trihydroxy-benzoate | 20 | 0.97 | 82.34 |
| 56 | Methyl 3,4,5-trihydroxy-benzoate | 10 | 0.47 | 82.60 |
| 57 | Methoxyhydroquinone | 10 | 0.90 | 77.17 |
| 58 | N-AcetylCysteine | 10 | 2.97 | 76.56 |
| 59 | Nordihydroguaiaretic Acid | 10 | 1.25 | 68.60 |
| 60 | 2Phenylbenzimidazole sulfonic acid | 30 | 0.30 | 78.37 |
| 61 | p-Coumaric Acid | 10 | 1.63 | 77.05 |
| 62 | 1,4-Phenylenediamine dihydrochloride | 10 | 1.58 | 79.04 |
| 63 | Propylgallate | 30 | 1.96 | 73.40 |
| 64 | Phthalic acid | 10 | 0.73 | 73.97 |
| 65 | α-(4-Pyridyl-N-oxide)N-tert-butylnitrone | 10 | 1.72 | 70.99 |
| 66 | Propylgallate | 10 | 0.38 | 84.45 |
| 67 | Pyridoxine | 100 | 1.95 | 72.53 |
| 68 | QuinicAcid | 100 | 1.79 | 68.36 |
| 69 | Quercetin | 1 | 0.50 | 77.43 |
| 70 | Rutin | 1 | 0.42 | 74.18 |
| 71 | Salicylate | 10 | 0.64 | 76.49 |
| 72 | Selenomethionine | 10 | 3.34 | 62.84 |
| 73 | Sodium Selenite | 30 | 1.46 | 78.66 |
| 74 | Sodium Sulfite | 10 | 0.63 | 75.84 |
| 75 | Spermine | 100 | 0.29 | 54.69 |
| 76 | Sulfanilic Acid | 10 | 1.57 | 76.47 |
| 77 | Syringic Acid | 10 | 1.12 | 82.32 |
| 78 | Tert-Butylhydroquinone | 10 | 1.33 | 84.93 |
| 79 | 4-Hydroxy-2,2,6,6-tetramethyl-piperidine 1-oxyl | 10 | 1.97 | 71.31 |
| 80 | Terephthalic acid | 10 | 0.86 | 74.54 |
| 81 | Tetrachloro-1,4-benzoquinone | 10 | 4.03 | 54.01 |
| 82 | 2,4,5-Trihydroxybutrophenone | 10 | 1.02 | 84.56 |
| 83 | 1,3,5-Tris(2-hydroxyethyl)isocyanurate | 10 | 1.75 | 76.86 |
| 84 | Thiourea | 100 | 15.31 | 51.62 |
| 85 | 2,2,6,6-Tetramethyl-4-piperidone | 10 | 1.89 | 69.38 |
| | hydrochloride | | | |
| 86 | 6-Hydroxy-2,5,7,8-tetramethyl-chroman-2-carboxylic acid | 10 | 0.84 | 74.97 |
| 87 | L-Tryptophan | 10 | 1.69 | 76.44 |

TABLE 2

| Entry number | Compound | Error Rate | cycle20 Int |
|---|---|---|---|
| 1 | Ethylgallate 10 mM + 10 mM Bis [2,2,6,6-Tetramethyl-4-piperidone] sebacate | 0.57 | 88.89 |
| 2 | Ethylgallate 10 mM + 10 mM Diethyldithiocarbamate | 0.50 | 90.48 |
| 3 | Ethylgallate 10 mM + 10 mM N,N-Diethylhydroxylamine | 0.49 | 69.01 |
| 4 | Ethylgallate 10 mM + 10 mM 2Phenylbenzimidazole sulfonic acid | 0.35 | 70.58 |
| 5 | Ethylgallate 10 mM + 10 mM Pyrogallol | 0.31 | 72.78 |
| 6 | Ethylgallate 10 mM + 25 mM NaAscorbate | 0.34 | 85.64 |
| 7 | Ethylgallate 10 mM + 30 mM Hydroquinone | 0.45 | 90.58 |
| 8 | Ethylgallate 10 mM + 50 mM Gallic Acid | 0.34 | 87.25 |
| 9 | gallic acid 100 mM + 250 mM mannitol | 0.31 | 77.08 |
| 10 | gallic acid 100 mM + 2M Urea | 0.17 | 80.90 |

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of detecting a nucleic acid having a fluorescent tag comprising:
 a) irradiating at least a portion of said nucleic acid with light, wherein said light comprises a suitable wavelength to induce a fluorescence emission;
 b) detecting said fluorescence emission; and
 c) repeating steps a) and b);
 wherein said irradiating step is carried out in the presence of a detection solution comprising gallic acid, a lower alkyl ester thereof, or mixtures thereof, and further comprising urea, said detection solution inhibiting light-induced degradation of said nucleic acid.

2. The method of claim 1, wherein said nucleic acid is in an array of nucleic acids attached to a support.

3. The method of claim 1, further comprising adding a fluorescently tagged nucleotide to said nucleic acid.

4. The method of claim 1, further comprising replacing a solution with said detection solution prior to the irradiation step.

5. The method of claim 2, wherein inhibiting light-induced degradation to said nucleic acid comprises reducing the cleavage of a nucleic acid member from said array.

6. The method of claim 1, wherein said gallic acid, said lower alkyl ester thereof, or said mixtures thereof is present in a concentration ranging from between about 10 mM to about 200 mM.

7. The method of claim 1, further comprising one or more compound(s), wherein said one or more compound(s) further enhances preservation of the integrity of said nucleic acid.

8. The method of claim 7, wherein said one or more compound(s) is selected from ascorbic acid or salt thereof, and isoascorbic acid or salt thereof.

9. The method of claim 1, comprising at least 50 cycles repeating step c.

10. The method of claim 1, comprising repeating said adding and detection steps for a number of cycles in a range from between about 100 cycles to about 1,000 cycles.

11. The method of claim 1, wherein the presence of said detection solution reduces a detection error rate by greater than 20% relative to a control.

12. The method of claim 11, wherein one or more compound(s) selected from ascorbic acid or salt thereof, and isoascorbic acid or salt thereof further reduce(s) said detection error rate.

13. The method of claim 1, wherein the presence of said detection solution reduces a detection error rate by greater than 40% relative to a control.

14. The method of claim 13, wherein one or more compound(s) selected from ascorbic acid or salt thereof, and isoascorbic acid or salt thereof further reduce(s) said detection error rate.

15. The method of claim 1, wherein the presence of said detection solution reduces a detection error rate by greater than 50% relative to a control.

16. The method of claim 15, wherein one or more compound(s) selected from ascorbic acid or salt thereof, and isoascorbic acid or salt thereof further reduce(s) said detection error rate.

17. The method of claim 1, wherein said irradiation step is conducted in a range from about 360 nm to about 700 nm.

18. The method of claim 1, wherein said irradiation step is conducted with a light source having power in a range between about 5 to about 500 milliwatts.

19. The method of claim 1, wherein said irradiation step is conducted for a time period of about 0.1 seconds to about 10 minutes.

20. The method of claim 2, wherein adding an additional fluorescently tagged nucleotide comprises using a polymerase to add a single nucleotide.

* * * * *